(12) United States Patent
Kirby et al.

(10) Patent No.: US 6,906,005 B2
(45) Date of Patent: Jun. 14, 2005

(54) HERBICIDAL COMPOSITIONS

(75) Inventors: Andrew Francis Kirby, Footscray (AU); Ashley Scott Martin, Brunswick (AU); Paul Leslie Griffiths, Newington (AU)

(73) Assignee: Huntsman Corporation Australia Pty Ltd (AU)

( * ) Notice: Subject to any disclaimer, the term of this patent is extended or adjusted under 35 U.S.C. 154(b) by 0 days.

(21) Appl. No.: 10/432,921

(22) PCT Filed: Nov. 30, 2001

(86) PCT No.: PCT/AU01/01557

§ 371 (c)(1),
(2), (4) Date: Sep. 22, 2003

(87) PCT Pub. No.: WO02/43492

PCT Pub. Date: Jun. 6, 2002

(65) Prior Publication Data

US 2004/0063586 A1 Apr. 1, 2004

(30) Foreign Application Priority Data

Dec. 1, 2000 (AU) .............................. PR1832

(51) Int. Cl.$^7$ .............................................. A01N 25/30
(52) U.S. Cl. ...................... 504/206; 504/226; 504/236; 504/243; 504/247; 504/250; 504/254; 504/260; 504/274; 504/310; 504/323; 504/324; 504/364
(58) Field of Search ................................ 504/206, 226, 504/236, 243, 247, 250, 254, 260, 274, 310, 323, 324, 364

(56) References Cited

U.S. PATENT DOCUMENTS 5,877,112 A * 3/1999 Roberts et al. ............. 504/206
6,248,695 B1 * 6/2001 Griffiths et al. ............ 504/206

* cited by examiner

Primary Examiner—S. Mark Clardy
(74) Attorney, Agent, or Firm—Christopher J. Whewell

(57) ABSTRACT

The present invention relates to surfactant systems and in particular herbicidal compositions comprising a water soluble herbicide and/or a salt thereof and a surfactant system, wherein the surfactant system comprises at least two surfactants selected from the group consisting of: i) alkyldiamine tetraalkoxylate surfactants; ii) N-alkyl alkyldiamine trialkoxylate surfactants; and iii) phosphated alcohol alkoxylate surfactants.

49 Claims, No Drawings

HERBICIDAL COMPOSITIONS

This invention relates to surfactant systems and in particular surfactant Systems useful in herbicide formulations. The invention also relates to herbicide formulations comprising the surfactant system and a method of controlling or eradicating unwanted plants and vegetation using the herbicide formulations containing the surfactant system.

Surfactant systems are important in herbicide compositions as promoters of wetting, spreading and penetration of the active agent. The surfactant system can affect efficacy of the herbicide composition and contribute to environmental effects such as aquatic toxicity and irritancy to skin and eyes.

The efficacy, aquatic toxicity and irritancy of water soluble herbicides, such as N-(phosphonomethyl)glycine (glyphosate), 4-[hydroxy(methyl)phosphinoyl]-DL-homoalanine (glufosinate), 1,1'-dimethyl-4,4'-bipyridinium dichloride (paraquat dichloride), 1,1'-ethylene-2,2'-bipyridyldiylium dibromide (diquat dibromide) and phenoxy acid herbicides can be affected by choice of surfactant system.

Some herbicide compositions include particular surfactant systems to enhance efficacy, however, these compositions often have undesirable properties such as unacceptable aquatic toxicity or irritancy. Some herbicidal compositions are formulated with particular surfactant systems to reduce aquatic toxicity or irritancy, but often at the expense of efficacy. There is a need for herbicidal compositions that exhibit acceptable aquatic toxicity and irritancy but not at the expense of efficacy of the compositions.

Glyphosate and its salts are well known non-selective systemic herbicides, first developed in the early 1970's by Monsanto Company. After absorption through the foliage it is rapidly translocated to regions of metabolic activity, including the roots and shoots. It has been found that formulations of glyphosate with some surfactant adjuvants can lead to enhancement of herbicidal activity.

Wyrill and Burnside, *Weed Science*, 25, (1977), 275–287, conducted a study of the effects of different surfactants on the herbicidal action of glyphosate. Some classes of surfactant were more effective than others in enhancing the herbicidal effect of glyphosate (in particular as a solution of the isopropylamine salt). Despite this study and subsequent attempts to correlate glyphosate activity enhancement with surfactant structure, the effectiveness of surfactants with glyphosate is variable and difficult to predict.

The most commonly used surfactant adjuvants in glyphosate formulations are the tallow amine ethoxylates. While these surfactants are very effective in enhancing the activity of glyphosate, they have recently been shown to have significant aquatic toxicity. Accordingly in many regions the use of glyphosate compositions comprising tallow amine ethoxylates in proximity to waterways and catchment areas has been severely regulated. In particular it has been shown that about 3 ppm of a standard ethoxylated tallow amine/glyphosate formulation has an acute toxic effect on *Daphnia carinata* according to a standard 48 hour $EC_{50}$ test.

Glyphosate compositions having surfactant systems including alkyldiamine tetraalkoxylate surfactants or an alkyldiamine tetraalkoxylate and an alkyl glycoside or alkylpolyglycoside surfactant were reported in WO 98/24313. While the surfactant system comprising alkyldiamine tetraalkoxylate and alkylpolyglycoside was found to have good efficacy, the inclusion of the alkylpolyglycoside may increase irritancy and cause unacceptable foaming in the herbicide composition.

N-alkyl amine ethoxylates and N-alkyl alkyldiamine trialkoxylates have been described in Wyrill and Burnside, *Weed Science*, 25, (1977), 275–287 and AU 57556/90. While these surfactants have been found to be efficacious, especially when used with glyphosate, they suffer from being aquatically toxic and skin and eye irritants Phosphated alcohol ethoxylate surfactants have been described in AU 641761. While these surfactants are known to be efficacious when used in glyphosate compositions and have low aquatic toxicity, their efficacy is not as good as other surfactants and they may be irritants unless the phosphate is fully neutralised.

It has been reported that the skin and eye irritancy of herbicide compositions may be reduced by using a combination of a phosphated alcohol alkoxylate surfactant and an alkyl amine ethoxylate surfactant as described in AU 653351. It appears that the reduction of irritancy results from the neutralising effect these surfactants have on one another. However, the large amount of alkylamine ethoxylate required results in increased aquatic toxicity.

It has now been surprisingly found that a surfactant system comprising at least two surfactants selected from the group consisting of alkyldiamine tetraalkoxylate surfactants, N-alkyl alkyldiamine trialkoxylate surfactants and phosphated alcohol alkoxylate surfactants, when used in a herbicide composition comprising a water soluble herbicide, provides not only efficacious compositions, but low aquatic toxicity and low irritancy to skin and eyes.

It has surprisingly been found that herbicide compositions comprising glyphosate and a surfactant system of the present invention have comparable efficacy over known and commonly used ethoxylated tallow amine compositions or the surfactants of the present surfactant system when used alone.

According to a first aspect of the invention there is provided a herbicidal composition comprising a water soluble herbicide and/or a salt thereof and a surfactant system, wherein the surfactant system comprises at least two surfactants selected from the group consisting of:
i) alkyldiamine tetraalkoxylate surfactants;
ii) N-alkyl alkyldiamine trialkoxylate surfactants; and
iii) phosphated alcohol alkoxylate surfactants.

According to a second aspect of the invention there is provided a use of a surfactant system comprising at least two surfactants selected from the group consisting of:
i) alkyldiamine tetraalkoxylate surfactants;
ii) N-alkyl alkyldiamine trialkoxylate surfactants; and
iii) phosphated alcohol alkoxylate surfactants;
as an adjuvant in a herbicide composition, wherein said herbicide composition comprises a water soluble herbicide.

According to a third aspect of the invention there is provided a method of controlling or eradicating unwanted plants or vegetation comprising the step of applying to a locus where control or eradication is desired, a phytotoxic amount of a herbicidal composition comprising a water soluble herbicide and a surfactant system, wherein the surfactant system comprises at least two surfactants selected from the group consisting of:
i) alkyldiamine tetraalkoxylate surfactants;
ii) N-alkyl alkyldiamine trialkoxylate surfactants; and
iii) phosphated alcohol alkoxylate surfactants.

According to a fourth aspect of the invention there is provided a surfactant system comprising at least two surfactants selected from the group consisting of:
i) alkyldiamine tetraalkoxylate surfactants;
ii) N-alkyl alkyldiamine trialkoxylate surfactants; and
iii) phosphated alcohol alkoxylate surfactants.

The term "low aquatic toxicity" is used herein in connection with the surfactants or herbicide compositions of the present invention to refer to an acute aquatic toxicity less than the toxicity of an equivalent composition comprising an ethoxylated tallow amine as the surfactant component. The term also indicates that the toxicity of the surfactant or composition is sufficiently low to satisfy local, regional or national regulations governing the toxicity of surfactants or herbicide compositions in the locality, region or country in which the surfactant or composition is used. The herbicide compositions according to the present invention preferably meet a standard $EC_{50}$ or $LC_{50}$ test in respect of a suitable indicator organism, for example Daphnia species such as *Daphnia carinata*, at a concentration of 100 ppm, more preferably 300 ppm, and most preferably 1000 ppm.

*Daphnia carinata* results have been quoted in most of our aquatic toxicity test results. Often, literature aquatic toxicity values are quoted for another water flea species, *Daphnia magna*, however this species cannot be imported into Australia for testing. It is accepted, but not confirmed, that *Daphnia carinata* may in fact be even more sensitive to surfactants than its "cousin".

As used herein, "water soluble herbicide" means a herbicide that is soluble in water under conditions of use, including conventional use rates and dilutions. For example, herbicides soluble in water at more than 1% weight per volume of composition.

Examples of water soluble herbicides suitable for use in the composition of the present invention include N-(phosphonomethyl)glycine (glyphosate), 4-[hydroxy(methyl)phosphinoyl]-DL-homoalanine (glufosinate), bipyridinium herbicides such as paraquat and diquat an salts thereof, amitrol, aromatic acid herbicides such as 2,4-D, MCPA, trichloropyr, pichloram, and bromoxynil and salts thereof.

Suitable cations for salts of glyphosate and glufosinate include alkali metal cations, such as sodium or potassium, and ammonium or substituted ammonium cations. The latter cations being derived from primary and secondary amines such as isopropylamine or dimethylamine and from diamines such as ethylene diamine.

Further, examples of agriculturally acceptable salts of glyphosate are trimethyl-sulfonium salt ("sulfosate") or aminoguanidine salts as disclosed in EP-A-0 088 180. Because glyphosate has more than one replaceable hydrogen atom, mono- and di-salts are possible, as well as mixtures of such salts. Typical glyphosate salts are the sodium, ammonium and trimethylsulphonium salts as well as the mixed alkylsulfonium salts and trialkyl salts.

A particularly useful salt of glufosinate is the ammonium salt.

Suitable anions for salts of bipyridinium herbicides include halide ions such as chloride and bromide ions.

Particularly useful cations for aromatic acid herbicides are ammonium and alkyl ammonium salts.

A particularly useful salt of bromoxynil is the potassium salt.

In a preferred embodiment the alkyldiamine tetraalkoxylate surfactant comprises a compound of formula (I):

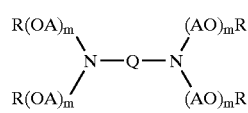
(I)

wherein Q is a linear or branched $C_1$–$C_6$ alkylene, each AO is independently an alkylene oxide unit, each m is independently an integer selected from 1 to 300 and each R is independently selected from hydrogen or an alkyl, acyl, benzyl or halide group.

Q is preferably —$(CH_2)_n$— wherein n is 2 to 6 or a branched alkylene group having 3 to 6 carbon atoms such as

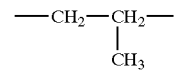

Most preferably Q is —$CH_2$—$CH_2$—.

AO is preferably a $C_1$–$C_4$ alkylene oxide unit, for example, ethylene oxide, propylene oxide or butylene oxide. Most preferably AO is an ethylene oxide unit or propylene oxide unit.

Preferably m is an integer from 1 to about 180, more preferably 8 to about 145.

Preferably R is hydrogen, methyl, acetyl or benzyl. Most preferably R is hydrogen.

$(AO)_m$ may be a polymer of alkylene oxide units in which each AO unit is the same or different. Preferably, $(AO)_m$ is a copolymer of ethylene oxide and propylene oxide units.

The alkylene oxide units may form homopolymers or copolymers, including block copolymers and random copolymers. For example, compounds of formula (I) may be made by starting with a compound of formula (II):

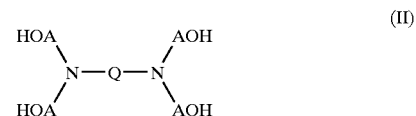
(II)

wherein Q is defined as in formula (I) and A is an alkylene group. The compound of formula (II) may then be condensed with an alkylene oxide unit wherein the alkylene group may be the same or different to A. The resulting compound may be further condensed with a different alkylene oxide unit and so on to give the final compound.

Preferably, these surfactants have the following formula (III):

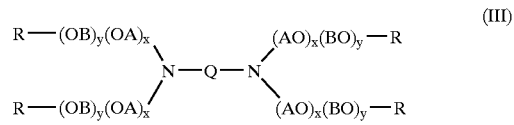
(III)

wherein Q is as defined in formula (I) and AO and BO are different $C_2$–$C_4$ alkylene oxide units, each R is independently H, $C_1$–$C_6$ alkyl, $C_2$–$C_4$ acyl, benzyl or halide, and each x and y is independently an integer from 0 to 150, provided x and y are not both zero.

Preferably AO is propylene oxide and BO is ethylene oxide, or AO is ethylene oxide and BO is propylene oxide. Where AO is propylene oxide and BO is ethylene oxide, x is preferably an integer from 1 to about 30, more preferably about 1 to about 25, and y is preferably 0 to about 150, more preferably about 4 to about 120.

A preferred alkyldiamine tetraalkoxylate surfactant has the following formula (IV):

$$\begin{array}{c} H(OC_2H_4)_y(OC_3H_6)_x \\ \phantom{H(OC_2H_4)_y(OC_3H_6)_x}\diagdown \\ \phantom{H(OC_2H_4)_y(OC_3H_6)_x}NCH_2CH_2N \\ \phantom{H(OC_2H_4)_y(OC_3H_6)_x}\diagup \\ H(OC_2H_4)_y(OC_3H_6)_x \end{array} \begin{array}{c} (C_3H_6O)_x(C_2H_4O)_yH \\ \diagup \\ \\ \diagdown \\ (C_3H_6O)_x(C_2H_4O)_yH \end{array} \quad (IV)$$

wherein x and y are as defined for formula (III).

Suitable alkyl diamine tetraalkoxylates which may be used as surfactants are the SYNPERONIC T™ series and TERIC 173™ which are commercially available ethylene diamine alkoxylates. TERIC 173™ is particularly suitable. TERIC 173™ is a compound of formula (IV) wherein x and y are 4. Also suitable are compounds of formula (IV) wherein x is 16 and y is 50 and compounds of formula (IV) wherein x is 22.5 and y is 118. Most suitable are compounds of formula (IV) wherein x is 1 and y is 4 or where x is 1 and y is 5.

In a preferred embodiment the N-alkyl alkyldiamine trialkoxylate surfactant comprises a compound of formula (V):

$$\begin{array}{c} R_2 \\ \diagdown \\ N-Q-N \\ \diagup \\ R_1(OA)_p \end{array} \begin{array}{c} (AO)_qR_1 \\ \diagup \\ \\ \diagdown \\ (AO)_rR_1 \end{array} \quad (V)$$

wherein Q is a linear or branched $C_1$–$C_6$ alkylene or $C_2$–$C_6$ alkenylene group, each AO is independently an alkylene oxide unit, p+q+r is the average moles of alkylene oxide units and is in the range of 5 to 25, each $R_1$ is independently hydrogen or an alkyl, acyl, benzyl or halide group and $R_2$ is a $C_8$–$C_{18}$ alkyl or $C_8$–$C_{18}$ alkenyl group.

Q is preferably —$(CH_2)_n$— wherein n is 2 to 6 or a branched alkylene group having 3 to 6 carbon atoms such as $$-CH_2-\underset{\underset{CH_3}{|}}{CH}-$$

Most preferably Q is —$CH_2$—$CH_2$—$CH_2$—.

AO is preferably a $C_1$–$C_4$ alkylene oxide unit, for example, ethylene oxide, propylene oxide or butylene oxide. Most preferably AO is ethylene oxide or propylene oxide.

Preferably p+q+r is an integer from 14 to 20 and most preferably from 16 to 18.

Preferably $R_1$ is selected from hydrogen, methyl, acetyl and benzyl. Most preferably $R_1$ is hydrogen.

Preferably $R_2$ is a $C_{12}$–$C_{18}$ is alkyl group and most preferably a $C_{16}$–$C_{18}$ alkyl group.

The alkylene oxide units may alternate in the chain. For example compounds of formula (V) may be made by starting with a compound of formula (VI):

$$\begin{array}{c} R_2 \\ \diagdown \\ N-Q-N \\ \diagup \\ HOA \end{array} \begin{array}{c} AOH \\ \diagup \\ \\ \diagdown \\ AOH \end{array} \quad (VI)$$

wherein Q is as defined in formula (V) and A is an alkylene group. The compound of formula (VI) may then be condensed with an alkylene oxide unit wherein the alkylene group may be the same or different to A. The resulting compound may be further condensed with a different alkylene oxide and so on to give the final compound.

Preferably, these surfactants have the following formula (VII):

$$\begin{array}{c} R_2 \\ \diagdown \\ N-Q-N \\ \diagup \\ H(OA)_p \end{array} \begin{array}{c} (AO)_qH \\ \diagup \\ \\ \diagdown \\ (AO)_rH \end{array} \quad (VII)$$

Q is —$(CH_2)_n$— wherein n is 2 to 6 or a branched alkylene group having 3 to 6 carbon atoms such as $$-CH_2-\underset{\underset{CH_3}{|}}{CH}-$$

Most preferably Q is —$CH_2$—$CH_2$—$CH_2$—; and wherein AO is an alkylene oxide unit in which A is selected from a straight chained $C_2$–$C_4$ alkylene group or a branched $C_2$–$C_4$ alkylene group such as $$-CH_2-\underset{\underset{CH_3}{|}}{CH}-$$

preferably AO is ethylene oxide.

p+q+r is in the range of 5 to 25, preferably 14 to 20 and most preferably 16 to 18.

$R_2$ is preferably a $C_{12}$–$C_{18}$ alkyl group and most preferably a $C_{16}$–$C_{18}$ alkyl group.

An example of a suitable N-alkyl alkyldiamine trialkoxylate is a compound of formula (VII) wherein Q is —$CH_2$—$CH_2$—$CH_2$—, A is —$CH_2$—$CH_2$—, p+q+r is 17 and $R_2$ is a $C_{16}$–$C_{18}$ alkyl group (N-tallow 1,3-propane diamine+17 moles of ethylene oxide).

In a preferred embodiment, the phosphated alcohol alkoxylate surfactant comprises a compound of the formula (VIII):

$$R_3-O-(AO)_s-\underset{\underset{O-M}{\diagdown}}{\overset{\overset{O-M}{\diagup}}{P}}=O \quad (VIII)$$

in which
$R_3$ represents a $C_4$–$C_{18}$ alkyl group,
AO is an alkylene oxide unit where A may be selected from straight chained $C_2$–$C_4$ alkylene group or a branched $C_2$–$C_4$ alkylene group such as $$-CH_2-\underset{\underset{CH_3}{|}}{CH}-$$

preferably AO is ethylene oxide,
s is an integer between 2 and 12, and
each M is independently selected from a hydrogen atom or a sodium atom or an ammonium or alkylammonium group.

Preferably, $R_3$ is an alkyl group having 12 to 14 carbon atoms and preferably s is 9 and M is hydrogen.

An example of a suitable phosphated alcohol alkoxylate surfactant is a compound of formula (VIII) where $R_3$ is a $C_{12}$–$C_{14}$ alkyl group, A is ethylene, s is 9 and M is hydrogen.

In one preferred aspect of the invention the surfactant system comprises an alkyldiamine tetraalkoxylate surfactant and an N-alkyl alkyldiamine trialkoxylate surfactant. The preferred ratio of alkyldiamine tetraalkoxylate to N-alkyl alkyldiamine trialkoxylate is at least 3:1. This system may further comprise an N-alkylamine alkoxylate surfactant having formula (IX):

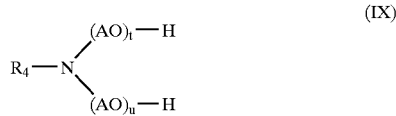

(IX)

wherein $R_4$ is a $C_{12}$–$C_{18}$ alkyl or $C_{12}$–$C_{18}$ alkenyl group, each AO is independently a $C_2$–$C_4$ alkylene oxide unit and t+u is the average moles of alkylene oxide units and is in the range of 5 to 20.

A suitable N-alkylamine alkoxylate surfactant is TERIC 17M15™ where $R_4$ is $C_{16}$–$C_{18}$ alkyl, AO is ethylene oxide and n is 15.

The ratio of alkyldiamine tetraalkoxylate to the combination of N-alkyl alkyldiamine trialkoxylate and N-alkylamine alkoxylate is preferably no less than 3:1.

In another aspect of the invention the surfactant system comprises an alkyldiamine tetraalkoxylate surfactant and a phosphated alcohol alkoxylate surfactant. The amount of phosphated alcohol alkoxylate added is sufficient to provide a neutral pH.

In another aspect of the invention, the surfactant system comprises an N-alkyl alkyldiamine trialkoxylate surfactant and a phosphated alcohol alkoxylate surfactant. The amount of phosphated alcohol alkoxylate added is sufficient to provide a neutral pH.

In yet another preferred aspect of the invention, the surfactant system comprises an alkyldiamine tetraalkoxylate surfactant, an N-alkyl alkyldiamine alkoxylate surfactant and a phosphated alcohol alkoxylate surfactant. The preferred ratio of alkyldiamine tetraalkoxylate surfactant to N-alkyl alkyldiamine trialkoxylate surfactant is at least 3:1. The phosphated alcohol alkoxylate is further added to give a neutral pH.

The final composition of this surfactant system is preferably 50–70% alkyldiamine tetraalkoxylate, 10–40% N-alkyl alkyldiamine trialkoxylate and 10–40% phosphated alcohol alkoxylate, weight per weight of surfactant system. Most preferably the composition contains 60% alkyldiamine tetraalkoxylate, 20% N-alkyl alkyldiamine alkoxylate and 20% phosphated alcohol alkoxylate, weight per weight of surfactant system.

If one surfactant in the surfactant system has a low level of alkoxylation, it is preferable that the other surfactant or surfactants in the system have a higher level of alkoxylation.

The compositions of the present invention may be in the form of solids, liquids or pastes. The compositions include both dilute compositions which are ready for immediate use and concentrated compositions which may require dilution before use. Therefore, the concentration of the active ingredient in the compositions of the present invention will vary depending on the type of formulation and whether the composition is ready for use such as, for example, a dust formulation or whether the composition is a concentrate such as, for example, a water soluble powder, a wettable powder or granule, which is suitable for dilution before use. In general the compositions of the present invention comprise from 1 ppm to 99% by weight of active ingredient.

The solid compositions may be in the form of powders, dusts, pellets, grains, and granules wherein the active ingredient and surfactant system are mixed with a solid diluent. Powders and dusts may be prepared by mixing or grinding the active ingredient and surfactant system with a solid carrier to give a finely divided composition. Granules, grains and pellets may be prepared by bonding the active ingredient and surfactant system to a solid carrier, for example by coating or impregnating the preformed granular solid carrier with the active ingredient or by agglomeration techniques.

Examples of solid carriers include mineral earths and clays such as, for example, kaolin, bentonite, kieselguhr, Fuller's earth, Attaclay, diatomaceous earth, bole, loess, talc, chalk, dolomite, limestone, lime, calcium carbonate, powdered magnesia, magnesium oxide magnesium sulfate, gypsum, calcium sulfate, prophyllite, silicic acid, silicates and silica gels; fertilizers such as, for example, ammonium sulfate, ammonium phosphate, ammonium nitrate and urea; natural products of vegetable origin such as, for example, grain meals and flours, bark meals, wood meals, nutshell meals and cellulosic powders; and synthetic polymeric materials such as, for example, ground or powdered plastics and resins.

A preferred liquid composition comprises an aqueous solution of the active ingredient or a dispersion of the parent acid form of the active ingredient, together with surfactant system which is suitable for application by spraying, atomizing or watering. Such aqueous compositions are generally prepared by mixing concentrated compositions with water. Suitable concentrated compositions include solutions, pastes, oil dispersions, aqueous suspensions and wettable powders. The concentrates are usually required to withstand storage to be capable of dilution with water to form aqueous preparations which remain homogenous for a sufficient time to enable them to be applied by conventional spray equipment. The concentrates conveniently contain from 20 to 80%, preferably 20 to 60%, by weight of active ingredient.

The surfactant system may also be added to a spray tank solution of herbicide, ie. be applied as a tank added solution. Most preferably the herbicidal compositions are liquid spray compositions.

The compositions of the present invention may also contain other conventional adjuvants normally formulated with herbicide formulations such as anti-foaming agents, thickeners, heat stabilizers, ultraviolet absorbers, dispersants and fertilisers, and other agriculturally acceptable materials, including fillers, such as talc, diatomaceous earth and the like, and diluents, such as water. The compositions may also contain additional surfactant adjuvants having low aquatic toxicity, and low irritancy, provided the presence of such surfactants does not reduce the efficacy of the herbicidal compositions below acceptable levels.

Furthermore, the compositions of the invention may be formulated so their properties, such as cloud point, are appropriate for their conditions of use.

The compositions of the present invention may be used in the control or eradication of unwanted plants or vegetation by application to a locus where control is desired. Normally the compositions are applied to foliage of the weed pests to be eradicated. A person skilled in the art would be able to determine the appropriate application rate depending on the herbicide, vegetation to be eradicated and the prevailing conditions when used.

The invention will now be described with reference to the accompanying examples which illustrate some preferred embodiments of the invention and some comparisons with commercial formulations. However, it is to be understood that the particularity of the following description is not to supersede the generality of the preceding description of the invention.

EXAMPLE 1

Formulation 1

A stable liquid glyphosate formulation was prepared by combining glyphosate (360 g/L acid, present as the isopropylamine salt), plus 150 g/L of a blend of surfactants having 25% w/w tallow propyldiamine plus 17 moles ethylene oxide and 75% w/w of ethylenediamine condensed with 4 moles of propylene oxide and 16 moles of ethylene oxide, then to volume with water.

Aquatic toxicity: 48 $EC_{50}$ (*Daphnia carinata*)=195 mg/L

EXAMPLE 2

Formulation 2

A stable liquid glyphosate formulation was prepared by combining glyphosate (360 g/L acid, present as the isopropylamine salt), plus 150 g/L of a blend of surfactants having 20% w/w tallow propyldiamine plus 17 moles ethylene oxide and 60% w/w of ethylenediamine condensed with 4 moles propylene oxide and 16 moles of ethylene oxide and 20% of a phosphated $C_{12}$–$C_{14}$ alcohol ethoxylate having 9 moles ethylene oxide, then to volume with water.

Aquatic toxicity: (Range finder result only) 48 $EC_{50}$ (*Daphnia carinata*)=60–130 mg/L.

EXAMPLE 3

Formulation 3

A stable liquid glyphosate formulation was prepared by combining glyphosate (490 g/L acid, present as the isopropylamine salt), plus 150 g/L of a blend of surfactants having 25% w/w tallow propyldiamine plus 17 moles ethylene oxide and 75% w/w of ethylenediamine condensed with 4 moles of propylene oxide and 16 moles of ethylene oxide, then to volume with water.

Efficacy Testing

Formulation 1 from Example 1, together with Formulations 2 and 3 were tested for efficacy against control samples containing 360 g/L (Control Formulation 1) or 490 g/L (Control Formulation 2) glyphosate (present as the isopropylamine salt) and 150 g/L tallow amine ethoxylate having 15 moles of ethylene oxide. The compositions were applied at 250 g ai/ha and 450 g ai/ha and the percentage weed control was assessed 14 days after spray application. The results are shown in Table 1.

TABLE 1

Percentage (%) control 14 days after spray application of glyphosate treatments applied at 250 and 450 g ai/ha.

| Formulation | Glyphosate dose (g ai/ha) | | |
|---|---|---|---|
| | 250 | 450 | Mean |
| Control Formulation 1 | 43[a] | 70[a] | 56[a] |
| Formulation 1 | 38[a] | 60[a] | 49[a] |
| Formulation 2 | 41[a] | 59[a] | 50[a] |
| Control Formulation 2 | 50[a] | 63[a] | 56[a] |
| Formulation 3 | 31[a] | 62[a] | 49[a] |
| Unsprayed control | | 0 | |
| LSD (P = 0.05) | | 22 | 15 |

Any column containing data followed by one or more of the same letters are not significantly different (P < 0.05)

It can be seen from the above results that the surfactant systems of the present invention have comparable efficacy to those known in the art.

EXAMPLE 4

Formulation 4

A stable liquid glyphosate formulation was prepared by combining glyphosate (490 g/L acid, present as the isopropylamine salt), plus 120 g/L of ethylenediamine plus 4 moles of propylene oxide and 16 moles of ethylene oxide, then to volume with water.

Aquatic toxicity: 48 hr $EC_{50}$ (*Daphnia carinata*)=766 mg/L

Efficacy was measured by assessing fresh weight reduction on annual ryegrass at 14 days after application. The control formulations contained 360 g/L glyphosate present as the isopropylamine salt and 170 g/L surfactant comprising ethylene diamine plus 4 moles of propyleneoxide and 16 moles of ethylene oxide and alkylpolyglucosides. The results are shown in Table 2.

TABLE 2

Bioefficacy data for surfactant systems in 360 g/L glyphosate.

| | $ED_{50}$ |
|---|---|
| Formulation 4 | 134 |
| Control Formulation 3 | 53 |
| Control Formulation 4 | 58 |
| Control Formulation 5 | 59 |
| Control Formulation 6 | 62 |

It can be seen from the results that alkyl diamine tetraalkoxylates have low aquatic toxicity but reduced efficacy when used as the only surfactant in herbicidal compositions.

EXAMPLE 5

Formulation 5

A commercial 450 g/L glyphosate formulation, containing a phosphated alcohol ethoxylate as the primary surfactant, was tested for efficacy against the industry standard 450 g/L glyphosate formulation.

Efficacy was measured by assessing % ryegrass control 21 days after application. The control formulation comprised a 450 g/L glyphosate formulation and a tallow amine ethoxylate surfactant having 15 moles of ethylene oxide The results are shown in Table 3.

TABLE 3 percentage control of ryegrass 21 days after application.

| | % control |
|---|---|
| Formulation 5 | 30 |
| Control Formulation 7 | 50 |

It can be seen from the above results that when phosphated alcohol ethoxylates are used as the only surfactant, the herbicide compositions have reduced efficacy.

EXAMPLE 6

Surfactant aquatic toxicity was measured for some surfactants alone. The results are shown in Table 4.

TABLE 4

| Surfactant | EC$_{50}$ (*Daphnia carinata*) 48 hrs (mg/L) |
|---|---|
| tallow propyldiamine + 5 moles ethylene oxide | 0.57 |
| tallow amine + 15 moles ethylene oxide | 3.0 |
| tallow propylamine + 14 moles ethylene oxide | 1–10 |

These surfactants alone have high aquatic toxicity.

EXAMPLE 7

Formulation 6

A stable liquid glyphosate formulation was prepared by combining glyphosate (360 g/L acid strength present as the isopropylamine salt) plus 150 g/L of a blend of surfactants having 25% w/w tallowpropyldiamine plus 17 moles of ethylene oxide and 75% w/w of ethylene diamine condensed with 4 moles of propylene oxide and 20 moles of ethylene oxide, then to volume with water.

EXAMPLE 8

Formulation 7

A stable liquid glyphosate formulation was prepared by combining glyphosate (360 g/L acid strength present as the isopropylamine salt) plus 150 g/L of a blend of surfactants having 20% w/w tallowpropyldiamine plus 17 moles of ethylene oxide and 60% w/w of ethylene diamine condensed with 4 moles of propylene oxide and 20 moles of ethylene oxide and 20% w/w of a phosphated $C_{12}$–$C_{14}$ alcohol ethoxylate having 9 moles of ethylene oxide, then to volume with water.

Formulation 6 from Example 7 and Formulation 7 from Example 8 were tested for irritancy together with Control Formulation 1 and Control Formulation 8 which is a 1% solution of sodium lauryl sulphate (SLS) as active matter.

The irritancy testing was carried out in vitro using the Zein Test. Zein testing is based on the solubility of a protein "zein" in surfactant or other solution and is expressed as mg of nitrogen/100 mL of sample. Zein testing is usually used as a first stage screening test due to its correlation with in vivo tests. The results are shown in Table 5 with the Zein Score assigned in mgN/100 mL.

TABLE 5 in vitro irritancy date for surfactant systems in 360 g/L glyphosate

| Formulation | Zein Score (mgN/100 mL Solution) |
|---|---|
| Formulation 6 | 14 |
| Formulation 7 | 10 |
| Control Formulation 1 | 28 |
| Control Formulation 8 | 473 |

As can be seen from this data, the irritancy score of the formulation of Example 7 and Example 8 are considerably reduced compared to that of the control formulations.

EXAMPLE 9

A stable liquid glyphosate formulation was prepared by combining glyphosate (360 g/L acid strength present as the isopropylamine salt) plus 150 g/L of a blend of surfactants having 25% w/w tallow propyldiamine plus 17 moles of ethylene oxide and 75% w/w of a phosphated $C_{12}$–$C_4$ alcohol ethoxylate having 9 moles of ethylene oxide, then to volume with water.

EXAMPLE 10

A stable liquid glyphosate formulation was prepared by combining glyphosate (360 g/L acid strength present as the isopropylamine salt) plus 150 g/L of a blend of surfactants having 60% w/w of ethylene diamine condensed with 4 moles of propylene oxide and 16 moles of ethylene oxide and 20% w/w of a phosphated $C_{12}$–$C_{14}$ alcohol ethoxylate having 9 moles of ethylene oxide, together with 20% w/w tallow amine condensed with 15 moles of ethylene oxide, then to volume with water.

EXAMPLE 11

A stable liquid glyphosate formulation was prepared by combining glyphosate (360 g/L acid strength present as the isopropylamine salt) plus 150 g/L of a blend of surfactants having 70% w/w of ethylene diamine condensed with 4 moles of propylene oxide and 16 moles of ethylene oxide and 30% w/w of a phosphated $C_{12}$–$C_{14}$ alcohol ethoxylate having 9 moles of ethylene oxide, then to volume with water.

EXAMPLE 12

A stable liquid paraquat formulation was prepared by combining paraquat dichloride (200 g/L strength present as the salt) plus 120 g/L of a blend of surfactants having 25% w/w tallow propyldiamine plus 17 moles of ethylene oxide and 75% w/w of ethylene diamine condensed with 4 moles of propylene oxide and 16 moles of ethylene oxide, then to volume with water. The formulation was buffered to acid pH, and minor amount of stench and emetic were added.

EXAMPLE 13

A stable liquid hormone ester formulation was prepared by combining 2,4-D amine (200 g/L strength present as the ammonium salt) plus 100 g/L of a blend of surfactants having 25% w/w tallow propyldiamine plus 17 moles of ethylene oxide and 75% w/w of ethylene diamine condensed with 4 moles of propylene oxide and 16 moles of ethylene oxide, then to volume with water.

EXAMPLE 14

A stable granular formulation was prepared by combining glyphosate (510 g/kg present as the ammonium salt) plus 150 g/L of a blend of surfactants having 25% w/w tallow propyldiamine plus 25 moles of ethylene oxide and 75% w/w of ethylene diamine condensed with 16 moles of propylene oxide and 50 moles of ethylene oxide, together with 150 g/L of powdered urea, then to weight with ammonium sulphate. The mixture was extruded with a minimal amount of water then dried to give granular composition which dissolved readily.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference to any prior art in this specification is not, and should not be taken as, an acknowledgment or any form of suggestion that that prior art forms part of the common general knowledge in Australia.

The claims defining the invention are as follows:

1. A herbicidal composition comprising a water soluble herbicide and/or a salt thereof and a surfactant system, wherein the surfactant system comprises at least two surfactants selected from the group consisting of:

i) alkyldiamine tetraalkoxylate surfactants;
   ii) N-alkyl alkyldiamine trialkoxylate surfactants; and
   iii) phosphated alcohol alkoxylate surfactants.

2. A herbicidal composition according to claim 1 wherein the surfactant system comprises an alkyldiamine tetraalkoxylate surfactant and an N-alkyl alkyldiamine trialkoxylate surfactant.

3. A herbicidal composition according to claim 1 wherein the surfactant system comprises an alkyldiamine tetraalkoxylate surfactant and a phosphated alcohol alkoxylate surfactant.

4. A herbicidal composition according to claim 1 wherein the surfactant system comprises an N-alkyl alkyldiamine trialkoxylate surfactant and a phosphated alcohol alkoxylate surfactant.

5. A herbicidal composition according to claim 1 wherein the surfactant system comprises an alkyldiamine tetraalkoxylate surfactant, an N-alkyl alkyldiamine trialkoxylate surfactant and a phosphated alcohol alkoxylate surfactant.

6. A herbicidal composition according to claim 1 wherein the alkyldiamine tetraalkoxylate surfactant comprises a compound of formula (I):

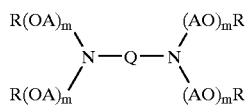

wherein Q is a linear or branched $C_1$–$C_6$ alkylene;

each AO is independently an alkylene oxide unit;

each m is independently an integer selected from 1 to 300; and each R is independently selected from hydrogen, alkyl acyl, benzyl or halide.

7. A herbicidal composition according to claim 6 wherein Q is —(CH2)$_n$— wherein n is 2 to 6, or a branched alkylene group having 3 to 6 carbon atoms.

8. A herbicidal composition according to claim 7 wherein Q is —$CH_2CH_2$—.

9. A herbicidal composition according to claim 6 wherein each AO is independently a $C_1$–$C_4$ alkylene oxide unit.

10. A herbicidal composition according to claim 9 wherein each AO is independently selected from ethylene oxide and propylene oxide.

11. A herbicidal composition according to claim 6 wherein m is an integer from 1 to about 180.

12. A herbicidal composition according to claim 11 wherein m is an integer from 8 to about 145.

13. A herbicidal composition according to claim 6 wherein R is hydrogen, methyl, acetyl or benzyl.

14. A herbicidal composition according to claim 13 wherein R is hydrogen.

15. A herbicidal composition according to claim 6 wherein the alkyldiamine tetraalkoxylate surfactant comprises a compound of formula (III):

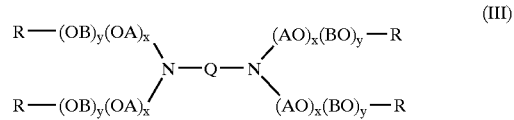

wherein AO and BO are different $C_2$–$C_4$ alkylene oxide units;

each R is independently hydrogen, $C_1$–$C_6$ alkyl, $C_2$–$C_4$ acyl, benzyl or halide; and each x and y is an integer from 0 to 50, provided that x and y are not both 0.

16. A herbicidal composition according to claim 15 wherein AO is propylene oxide, BO is ethylene oxide, x is an integer from 1 to 30 and y is an integer from 0 to 150.

17. A herbicidal composition according to claim 6 wherein the alkyldiamine tetraalkoxylate surfactant comprises a compound of formula (IV):

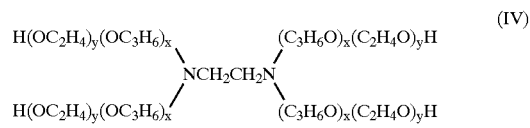

wherein x and y are integers from 0 to 150, provided that x and y are not both 0.

18. A herbicidal composition according to claim 1 wherein the N-alkyl alkyldiamine trialkoxylate surfactant comprises a compound of formula (V):

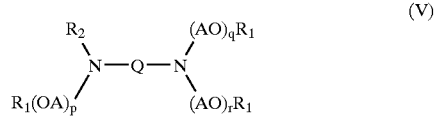

wherein Q is a linear or branched $C_1$–$C_6$ alkylene or $C_2$–$C_6$ alkenylene group;

each AO is independently an alkylene oxide unit;

p+q+r is the average moles of alkylene oxide units and is an integer selected from 5 to 25;

$R_1$ is independently selected from hydrogen, alkyl, acyl, benzyl or halide; and $R_2$ is a $C_8$–$C_{18}$ alkyl or $C_8$–$C_{18}$ alkenyl group.

19. A herbicidal composition according to claim 18 wherein Q is —$CH_2$)$_n$— wherein n is 2 to 6, or a branched alkylene group having 3 to 6 carbon atoms.

20. A herbicidal composition according to claim 19 wherein Q is —$CH_2$—$CH_2$—$CH_2$—.

21. A herbicidal composition according to claim 18 wherein each AO is independently a $C_1$–$C_4$ alkylene oxide unit.

22. A herbicidal composition according to claim 21 wherein each AO is independently selected from ethylene oxide and propylene oxide.

23. A herbicidal composition according to claim 18 wherein p+q+r is an integer from 14 to 20.

24. A herbicidal composition according to claim 23 wherein p+q+r is an integer from 16 to 18.

25. A herbicidal composition according to claim 18 wherein $R_1$ is selected from hydrogen, methyl, acetyl and benzyl.

26. A herbicidal composition according to claim 25 wherein $R_1$ is hydrogen.

27. A herbicidal composition according to claim 18 wherein $R_2$ is a $C_{12}$–$C_{18}$ alkyl group.

28. A herbicidal composition according to claim 27 wherein $R_2$ is a $C_{12}$–$C_{18}$ alkyl group.

29. A herbicidal composition according to claim 18 wherein the N-alkyl alkyldiamine trialkoxylate surfactant comprises a compound of formula (VII):

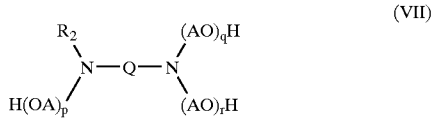

(VII)

wherein Q is —$(CH_2)_n$— wherein n is 2 to 6 or a branched alkylene group having 3 to 6 carbon atoms;

AO is a straight chain $C_2$–$C_4$ alkylene oxide unit or a branched $C_2$–$C_4$ alkylene oxide unit;

p+q+r is in the range of 5 to 25; and $R_2$ is a $C_{12}$–$C_{18}$ alkyl group.

30. A herbicidal composition according to claim 29 wherein Q is —$CH_2$—$CH_2$—$CH_2$—.

31. A herbicidal composition according to claim 29 wherein AO is ethylene oxide.

32. A herbicidal composition according to claim 29 wherein p+q+r is in the range of 14 to 20.

33. A herbicidal composition according to claim 32 wherein p+q+r is in the range of 16 to 18.

34. A herbicidal composition according to claim 29 wherein $R_2$ is a $C_{16}$–$C_{18}$ alkyl group.

35. A herbicidal composition according to claim 29 wherein the N-alkyl alkyldiamine trialkoxylate surfactant is a compound of formula (VII) wherein Q is —$CH_2$—$CH_2$—$CH_2$—, AO is ethylene oxide, p+q+r is 17 and $R_2$ is a $C_{16}$–$C_{18}$ alkyl group.

36. A herbicidal composition according to claim 1 wherein the phosphated alcohol alkoxylate comprises a compound of the formula (VIII):

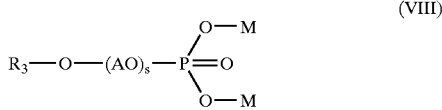

(VIII)

wherein $R_3$ is a $C_4$–$C_{18}$ alkyl group;

AO is a straight chain $C_2$–$C_4$ alkylene oxide unit or a branched $C_2$–$C_4$ alkylene oxide unit;

s is an integer between 2 and 12; and each M is independently selected from a hydrogen atom, a sodium atom or an ammonium or alkyl ammonium group.

37. A herbicide composition according to claim 36 wherein AO is ethylene oxide.

38. A herbicide composition according to claim 36 wherein $R_3$ is a $C_{12}$–$C_{14}$ alkyl group, AO is ethylene oxide, s is 9 and M is hydrogen.

39. A herbicide composition according to claim 2 wherein the surfactant system further comprises an N-alkylamine alkoxylate of formula (IX):

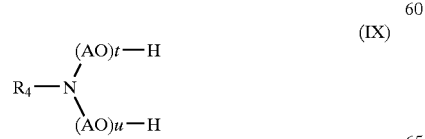

(IX)

wherein $R_4$ is a $C_{12}$–$C_{14}$ alkyl or $C_{12}$–$C_{14}$ alkenyl group;

each AO is independently a $C_2$–$C_4$ alkylene oxide unit; and t+u is the average moles of alkylene oxide units and is in the range of 5 to 20.

40. A herbicidal composition according to claim 1 wherein the ratio of alkyldiamine tetraalkoxylate to N-alkyl alkyldiamine trialkoxylate is at least 3:1.

41. A herbicidal composition according to claim 39 wherein the ratio of alkyldiamine tetraalkoxylate to the combination of N-alkyl alkyldiamine trialkoxylate and N-alkylamine alkoxylate is at least 3:1.

42. A herbicidal composition according to claim 5 comprising 50–70% alkyldiamine tetraalkoxylate, 10–40% N-alkyl alkyldiamine trialkoxylate and 10–40% phosphated alcohol alkoxylate, weight per weight of the surfactant system.

43. A herbicidal composition according to claim 42 comprising 60% alkyldiamine tetraalkoxylate, 20% N-alkyl alkyldiamine trialkoxylate and 20% phosphated alcohol alkoxylate, weight per weight of the surfactant system.

44. A herbicidal composition comprising:
a) a water soluble herbicide and/or salt thereof, wherein the water soluble herbicide is selected from the group consisting of: N-(phosphonomethyl)glycine (glyphosate), 4-[hydroxy(methyl)phosphinoyl]-DL-homoalanine (glufosinate), bipyridinium herbicides, amitrol, aromatic acid herbicides, and bromoxynil, and salts thereof; and
b) a surfactant system which comprises at least two surfactants selected from the group consisting of:
i) alkyldiamine tetraalkoxylate surfactants;
ii) N-alkyl alkyldiamine trialkoxylate surfactants; and
iii) phosphated alcohol alkoxylate surfactants.

45. A herbicidal composition according to claim 44 wherein the water soluble herbicide is N-(phosphonomethyl)glycine or salts thereof.

46. Use of a surfactant system comprising at least two surfactants selected from the group consisting of:
i) alkyldiamine tetraalkoxylate surfactants;
ii) N-alkyl alkyldiamine trialkoxylate surfactants; and
iii) phosphated alcohol alkoxylate surfactants;

as an adjuvant in a herbicide composition, wherein said herbicide composition comprises a water soluble herbicide.

47. A method of controlling or eradicating unwanted plants or vegetation comprising the step of applying to a locus where control or eradication is desired, a phytotoxic amount of a herbicidal composition comprising a water soluble herbicide and a surfactant system, wherein the surfactant system comprises at least two surfactants selected from the group consisting of:
i) alkyldiamine tetraalkoxylate surfactants;
ii) N-alkyl alkyldiamine trialkoxylate surfactants; and
iii) phosphated alcohol alkoxylate surfactants.

48. A surfactant system comprising at least two surfactants selected from the group consisting of:
i) alkyldiamine tetraalkoxylate surfactants;
ii) N-alkyl alkyldiamine trialkoxylate surfactants; and
iii) phosphated alcohol alkoxylate surfactants.

49. A herbicidal composition according to claim 44 wherein the aromatic acid herbicide is selected from the group consisting of: MCPA, triclopyr, and picloram.

* * * * *